United States Patent [19]

Takewaki et al.

[11] Patent Number: 5,569,803
[45] Date of Patent: Oct. 29, 1996

[54] METHOD FOR PRODUCING A CYCLOOLEFIN

[75] Inventors: Takahiko Takewaki; Naoko Fujita; Toshiharu Yokoyama, all of Yokohama; Takao Maki, Fujisawa, all of Japan

[73] Assignee: Mitsubishi Chemical Corporation, Tokyo, Japan

[21] Appl. No.: 363,034

[22] Filed: Dec. 23, 1994

[30] Foreign Application Priority Data

Dec. 24, 1993 [JP] Japan ................................. 5-328456
Jan. 11, 1994 [JP] Japan ................................. 6-001179
Feb. 28, 1994 [JP] Japan ................................. 6-029804

[51] Int. Cl.$^6$ ................................................. C07C 5/11
[52] U.S. Cl. ...................... 585/269; 585/266; 585/271; 585/273; 585/275; 585/277; 502/325; 502/349
[58] Field of Search ......................... 585/266, 269, 585/271, 273, 275, 277; 502/325, 349

[56] References Cited

U.S. PATENT DOCUMENTS

| | | | |
|---|---|---|---|
| 3,912,787 | 10/1975 | Nowack et al. | 585/272 |
| 4,055,512 | 10/1977 | Kageyama et al. | 502/74 |
| 4,392,001 | 7/1983 | Don et al. | 585/269 |
| 4,495,373 | 1/1985 | Niwa et al. | 585/269 |
| 4,575,572 | 3/1986 | Ichihashi et al. | 585/266 |
| 4,665,274 | 5/1987 | Ichihashi et al. | 585/267 |
| 4,678,861 | 7/1987 | Mitsui et al. | 585/266 |
| 4,734,536 | 3/1988 | Nagahara et al. | 585/269 |
| 5,157,179 | 10/1992 | Setoyama et al. | 585/266 |
| 5,334,790 | 8/1994 | Richard et al. | 585/271 |
| 5,414,171 | 5/1995 | Richard et al. | 585/271 |

FOREIGN PATENT DOCUMENTS

| | | |
|---|---|---|
| 0466128 | 1/1992 | European Pat. Off. . |
| WO93/16971 | 9/1993 | WIPO . |
| WO93/16972 | 9/1993 | WIPO . |

*Primary Examiner*—Anthony McFarlane
*Assistant Examiner*—Walter D. Griffin
*Attorney, Agent, or Firm*—Oblon, Spivak, McClelland, Maier & Neustadt, P.C.

[57] ABSTRACT

A method for producing a cycloolefin, which comprises partially hydrogenating a monocyclic aromatic hydrocarbon in the presence of water and a ruthenium catalyst supported on silica modified by zirconium oxide.

18 Claims, 7 Drawing Sheets

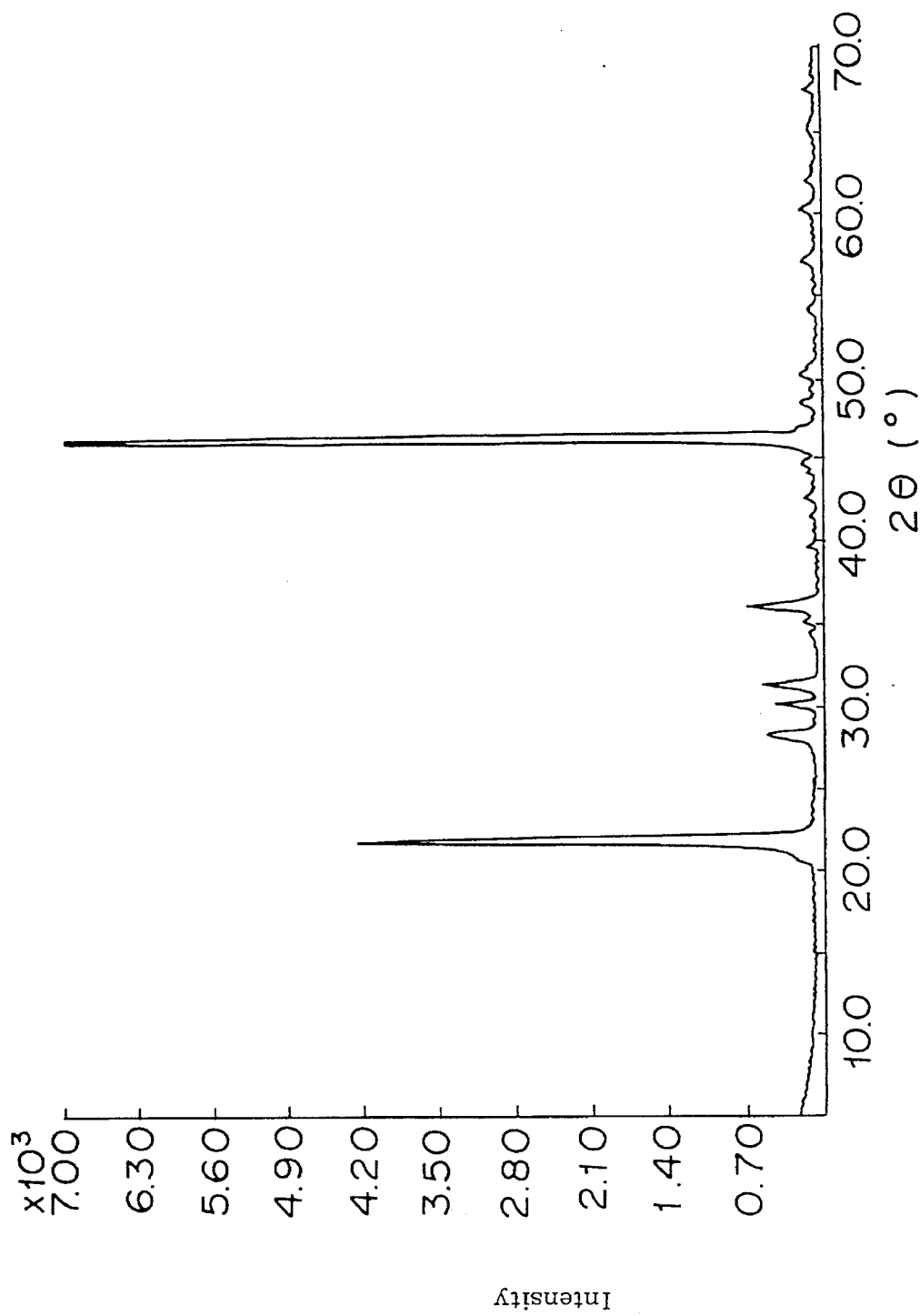

METHOD FOR PRODUCING A CYCLOOLEFIN

The present invention relates to a method for producing a cycloolefin which comprises partially hydrogenating monocyclic aromatic hydrocarbons to form the corresponding cycloolefins, particularly cyclohexene.

Cycloolefins are important intermediate compounds for lactams, dicarboxylic acids as starting materials for polyamides, lysines, medicines and agricultural chemicals.

Heretofore, a number of methods have been known with respect to methods for the production of cycloolefins, such as partial hydrogenation of monocyclic aromatic hydrocarbons, dehydration of cycloalkanols and dehydrogenation and oxidative dehydrogenation of cycloalkanes. Especially, if a cycloolefin can be produced efficiently by partially hydrogenating a monocyclic aromatic hydrocarbon, the reaction process can be the most simplified, such being desirable from viewpoint of the industrial process.

As a method for producing a cycloolefin by partially hydrogenating a monocyclic aromatic hydrocarbon, it is common to employ a method wherein ruthenium metal is mainly used as a catalyst and hydrogenation reaction is conducted in the presence of water and a metal salt. For such a ruthenium catalyst, many proposals have been made, such as a method wherein fine metal ruthenium particles are used by themselves (e.g. Japanese Unexamined Patent Publications No 50930/1986, No. 45541/1987 and No. 45544/1987), and a method wherein a catalyst having ruthenium supported on a carrier such as silica, alumina, barium sulfite or zirconium silicate, is used (e.g. Japanese Unexamined Patent Publications No. 130926/1982, No. 40226/1986 and No. 74141/1992).

However, each of such conventional methods has some problems and is not necessarily advantageous from the industrial viewpoint. The problems may, for example, be such that the selectivity for the desired cycloolefin is not adequate, that the catalytic activity is so low that it is difficult to produce the cycloolefin efficiently, that the durability of the catalyst is inadequate, and that handling efficiency of the catalyst is poor.

Further, in many conventional methods, it is necessary to add an additive such as a metal salt, an acid or an alkali to the reaction system. Such an additive not only makes the reaction system complicated, but accelerates corrosion of the reactor, or consumption or deterioration of the catalyst. Therefore, from the industrial point of view, a method is desired wherein no such an additive is incorporated.

The present inventors have conducted extensive researches to solve the above problems and as a result, have found that a catalyst having ruthenium supported on silica modified by zirconium oxide, is extremely effective for partial hydrogenation of a monocyclic aromatic hydrocarbon. The present invention has been accomplished on the basis of such a discovery.

Thus, the present invention provides a method for producing a cycloolefin, which comprises partially hydrogenating a monocyclic aromatic hydrocarbon in the presence of water and a ruthenium catalyst supported on silica modified by zirconium oxide.

Now, the present invention will be described in detail with reference to the preferred embodiments.

The carrier for the catalyst to be used in the present invention is silica modified by zirconium oxide. In the carrier for the catalyst to be used in the present invention, the type of silica is not particularly limited. However, it is usual to employ spherical silica. The particle size of the spherical silica may be selected appropriately taking into consideration, for example, the handling efficiency in the reaction system. For example, in the case of a suspension bed system, the particles size is usually preferably from 5 to 500 μm. The specific surface area of the carrier is not particularly limited and is usually from 3 to 200 $m^2/g$, preferably from 5 to 150 $m^2/g$. Further, the silica carrier preferably has pores such that when the pore volume and the pore size distribution are measured by a mercury injection method, the volume of pores having pore diameters of from 250 to 1,500 Å is at least 55%, preferably at least 60%, of the total pore volume of pores having pore diameters of from 75 to 150,000Å, and particularly preferably, the volume of pores having pore diameters of from 350 to 1,500 Å is at least 55% of the total pore volume. If the proportion of pores having pore diameters of less than 250 Å, is too large, the selectivity tends to be low. On the other hand, if the proportion of pores having pore diameters exceeding 1,500 Å, is too large, the activity tends to be low, such being undesirable. Further, silica having physical properties within such a range, has a characteristic such that in the process for preparation of the catalyst, it is hardly crystallized even when baking is carried out at a high temperature of a level of e.g. from 600° to 1,200° C.

The silica carrier modified by zirconium oxide to be used in the present invention, is a silica carrier having zirconium oxide supported in a highly dispersed state not only on the outer surface of silica but over the entire surface including the surface in the pores. "Supported in a highly dispersed state" means a state where crystallite sizes of supported zirconia are relatively small, and the crystallites are uniformly dispersed over the entire surface of silica. In such a case, the average crystallite size of zirconium oxide is usually from 10 to 200 Å, preferably from 20 to 100 Å. Here, the average crystallite size is the one which is calculated, for example, by the Scherrer formula from the broadening of the diffraction width at a diffraction angle (2θ) of zirconium oxide of about 30° as measured by powder X-ray diffraction method.

The amount of modifying zirconium oxide is not particularly limited so long as zirconium oxide is supported in a highly dispersed state on silica, but is usually from 0.1 to 20 wt %, preferably from 0.5 to 10 wt %, relative to the silica. If the amount is less than 0.1 wt %, no adequate modifying effect by zirconium oxide will be obtained, and such is not effective for the partial hydrogenation reaction. On the other hand, if it exceeds 20 wt %, the selectivity for a cycloolefin is likely to be low, and such is not necessarily effective for the partial hydrogenation reaction, and the cost for the carrier tends to be high, such being economically disadvantageous.

As a method for preparing the carrier in the present invention, any method may be employed so long as it is a method wherein zirconium oxide can be supported in a highly dispersed state on the silica surface, as described above. However, it is usually difficult to attain such a state by a method wherein silica and zirconium oxide are simply physically mixed. Therefore, it is usual to employ a method wherein using a solution having a zirconium compound dissolved in water or in an organic solvent, or a solution having a zirconium compound dissolved and then partially or entirely hydrolyzed with an alkali or the like, zirconium is supported on silica by a conventional impregnation method or a dip coating method, followed by drying and baking. The zirconium compound to be used here may, for example, be a halide, oxyhalide, nitrate, oxynitrate or hydroxide of zirconium, a complex compound such as an acetylacetonate complex of zirconium, or a zirconium alkoxide. The baking temperature may be at any level so long as the zirconium compound used can be converted to zirconium oxide. The temperature is usually at least 600° C., preferably from 800° to 1,200° C. However, if the baking is conducted at a temperature exceeding 1,200° C., crystallization of silica tends to be remarkable, whereby the catalytic activities tend to be low, such being undesirable.

Preparation of the catalyst can be conducted in accordance with a common method for preparation of a usual supported metal catalyst. Namely, a known supporting method can suitably be employed such as an evaporation to dryness method wherein the carrier is dipped in a solution of the catalyst component and then the solvent is evaporated with stirring to fix the active component, a spray method wherein a solution of the catalytically active component is sprayed while maintaining the carrier in a dry state, or a method wherein the carrier is dipped in a solution of the catalytically active component, followed by filtration.

The starting material for ruthenium as the catalytically active component may, for example, be a halide, nitrate, hydroxide or oxide of ruthenium, ruthenium carbonyl, a complex compound such as a ruthenium ammine complex, or a ruthenium alkoxide. As a solvent to be used for supporting the active component at the time of preparation of the catalyst, water or an organic solvent such as an alcohol, acetone, tetrahydrofuran, hexane or toluene may, for example, be used.

Ruthenium as the active component of the catalyst may be used alone. Otherwise, it may be used as supported together with other metal components. In such a case, the component to be supported together with ruthenium may, for example, be zinc, iron, cobalt, manganese, gold, lanthanum or copper. Such a metal compound which is used as a component to be supported together with ruthenium, may be a halide, nitrate, acetate or sulfate of such a metal, or a complex compound containing such a metal. Such an additional component may be supported on the carrier at the same time as the ruthenium material or may be supported after supporting ruthenium first. Otherwise, such a metal is first supported and then ruthenium may be supported.

With the catalyst prepared in such a manner, it is common to reduce and activate ruthenium before its use. As the reducing agent, a conventional reducing agent such as hydrogen, carbon monoxide, alcohol vapor, hydrazine, formalin or sodium borohydride can be used. It is preferred to employ hydrogen, and activation is conducted usually under a condition of from 80° to 500° C., preferably from 100° to 450° C. If the reduction temperature is less than 80° C., the reduction rate of ruthenium tends to be remarkably low. On the other hand, if it exceeds 500° C., aggregation of ruthenium tends to occur, whereby the yield and selectivity in the formation of the cycloolefin tend to be low.

It is possible to activate the catalyst also by subjecting the prepared catalyst to contact treatment with a certain specific metal salt. The metal salt to be used may, for example, be a salt of metal such as Group I element such as lithium, sodium or potassium, Group II element, such as magnesium, calcium or strontium, or manganese, iron, cobalt, zinc, copper, gold or zirconium, for example, a weak acid salt such as a carbonate or acetate, or a strong acid salt such as a hydrochloride, sulfate or nitrate. The contact treatment may be carried out by immersing the catalyst in an aqueous solution containing usually from 0.01 to 100 times by weight, preferably from 0.1 to 10 times by weight of the metal salt. The concentration of the metal salt in the aqueous solution is usually from $1 \times 10^5$ to 1 time by weight, preferably from $1 \times 10^{-4}$ to 0.2 time by weight, relative to water.

With respect to the treating conditions, the treatment is carried out usually under atmospheric pressure or elevated pressure usually at a temperature of from room temperature to 250° C., preferably from room temperature to 200° C., usually for from 10 minutes to 20 hours, preferably for from 1 to 10 hours. The atmosphere for treating the catalyst is usually an inert gas atmosphere or a hydrogen gas atmosphere, preferably a hydrogen gas atmosphere. After the contact treatment, the catalyst is separated usually by filtration from the aqueous metal salt solution used for the treatment, washed with water and dried for use. Further, after the drying, it may be further subjected to reduction treatment under a hydrogen gas atmosphere to further increase the catalytic activities.

In the above catalyst, the amount of ruthenium supported is usually from 0,001 to 10 wt %, preferably from 0.05 to 5 wt %, based on the silica carrier modified by zirconium oxide. When an additional metal component such as zinc, iron, cobalt, manganese, gold, lanthanum or copper is used together with ruthenium, the atomic ratio of such an additional metal component to ruthenium is selected usually within a range of from 0.01 to 20, preferably from 0.05 to 10.

Various factors may be considered as a reason why the zirconium oxide-modified silica carrier used in the catalyst of the present invention provides an especially effective performance in partial hydrogenation reaction as compared with a usual silica carrier not modified by zirconium oxide. Such an effective performance is believed to be attributable to the fact that by the modification of the silica surface by zirconium oxide, it has been made possible to uniformly disperse and support ruthenium as the main component of the catalyst.

With a conventional carrier, particularly silica having a relatively small specific surface area at a level of not more than 100 m²/g, non-uniform support such as aggregation of the catalyst component or segregation thereof in the vicinity of the surface, is likely to result. Whereas, with the carrier of the present invention having the surface of silica modified by zirconium oxide, it is possible to attain uniformly dispersed support even in such a case.

The dispersion of the catalyst component in the supported state can be analyzed by EPMA (X-ray microanalyzer). The dispersion of the catalyst component in the supported state can be usually expressed by an element distribution map of EPMA, but can be quantitatively represented by a line analysis method by EPMA. Namely, a catalyst particle which can be approximated to a spherical shape is cut along the plane containing the center of the catalyst particle, and the X-ray intensity of catalyst component (ruthenium) is measured at various points of the cross section to obtain the relative intensity ($I_n/I_{center}$) at each measured point to the intensity ($I_{center}$) of its center, and to obtain the frequency distribution of the relative intensity. If the dispersion of the catalyst component in the supported state is uniform, the frequency distribution tends to converge to the vicinity of $I_n/I_{center}=1$. If it is not uniform, the relative intensity may likely be large, and the width of the frequency distribution tends to broaden.

The uniform dispersion of the catalyst component in the supported state of the catalyst of the present invention may be expressed by the above mentioned line analysis method by EPMA as follows. Firstly, the maximum relative intensity is usually at most 4, preferably at most 3, more preferably at most 2.5. If the maximum relative intensity exceeds 4, ruthenium as the catalyst component is segregated e.g. at the outer surface of the carrier and is not uniformly dispersed, and such a state corresponds to the case where silica is used alone, or a physical mixture of silica and zirconium oxide is used as the carrier for the catalyst. Further, the catalyst of the present invention has a frequency distribution of at least 60%, preferably at least 70%, of the total within a relative intensity range of from 0.6 to 1.4. More preferably, it has a frequency distribution of at least 65% of the total within a relative intensity range of from 0.8 to 1.2.

The uniform dispersion in the supported state of the catalyst component as described above is believed to be effective not only for improving the selectivity for a cycloolefin and improving the activity per ruthenium, but also for improving peeling resistance of ruthenium, prevention of sintering and elongation of the effective life of the catalyst. Further, by the modification of the surface of silica by zirconium oxide, the mechanical strength is increased, whereby in the case of e.g. a suspension bed reaction, abrasion resistance will be improved. With the carrier for the catalyst used in the present invention, the stability at high temperatures is remarkable, and it is stable even under such heat treatment conditions that crystallization of silica or transformation of zirconium oxide results in the case of silica alone or in the case of a physical mixture of silica and zirconium oxide.

In the present invention, water is present in the reaction system. The amount of water present is usually from 0.01 to 10 times, preferably from 0.1 to 5 times by volume ratio to the aromatic hydrocarbon. Further, it is usual to employ a method wherein in addition to the catalyst component, a metal salt is present in the reaction system. As such a metal salt, a metal salt of an element of Group I of the periodic system such as lithium, sodium or potassium, an element of Group II such as magnesium, calcium or strontium, or manganese, iron, cobalt, zinc or copper, may, for example, be mentioned. Among them, salts of zinc, cobalt and lithium are particularly preferred. As the type of the metal salt, a salt of a weak acid such as a carbonate or acetate, or a salt of a strong acid such as a hydrochloride, sulfate or nitrate may, for example, be mentioned. The amount of the metal salt present is usually from $1\times10^{-5}$ to 1 time by weight, preferably from $1\times10^{-4}$ to 0.1 time by weight, relative to the coexisting water.

On the other hand, when the catalyst of the present invention is used, it is possible to obtain a good reaction result even if an additive such as a metal salt is not added to the reaction system. In general, in a reaction system containing an additive such as a metal salt, there is a tendency such that the catalytic activity per ruthenium metal tends to remarkably decrease when the amount of zirconium oxide for modifying silica is little. In a system where the catalyst of the present invention is used and an additive such as a metal salt is not contained, there is a tendency such that the catalytic activity is maintained at a high level even when the amount of zirconium oxide for modification is decreased. In a reaction system containing no metal salt, there is a general tendency such that the selectivity in the partial hydrogenation reaction slightly decreases as compared with the reaction system containing a metal salt. However, since the catalyst activity is very high, it is possible to efficiently obtain the desired product in a simple reaction system and under such a condition that corrosion of the reactor is little.

The monocyclic monoaromatic hydrocarbon to be treated by the present invention may, for example, be benzene, toluene, xylene or a benzene substituted by a lower alkyl group having from 1 to 4 carbon atoms. With respect to the reaction conditions of the present invention, the reaction temperature is selected usually within a range of from 50° to 250° C., preferably from 100° to 220° C. If the temperature is higher than 250° C., the selectivity for a cycloolefin tends to be low, and if it is less than 50° C., the reaction rate tends to be substantially low. The hydrogen pressure at the time of the reaction is selected usually within a range of from 0.1 to 20 MPa, preferably from 0.5 to 10 MPa. If the pressure exceeds 20 MPa, such is usually disadvantageous from the industrial point of view. On the other hand, if the pressure is less than 0.1 MPa, the reaction rate tends to be substantially low, and such is uneconomical from the viewpoint of the installation cost. The reaction may be carried out in a gas phase or in a liquid phase. Preferred is a liquid phase reaction. The reaction system is not particularly limited, and the reaction can be conducted in a batch system using a single reactor or two or more reactors, or can be conducted continuously.

In the accompanying drawings:

FIG. 7 is a powder X-ray diffraction pattern when the physical mixture of silica and zirconium oxide used for the catalyst in Comparative Example 2 was cooled from 1,200° C. to 200° C.

Now, the present invention will be described in further detail with reference to Examples. However, it should be understood that the present invention is by no means restricted by such specific Examples. In the following Examples and Comparative Examples, the conversion and the selectivity are defined by the following formulas.

$$\text{Conversion (\%)} = \frac{\text{Mols of the monocyclic aromatic hydrocarbon consumed by the reaction}}{\text{Mols of the monocyclic aromatic hydrocarbon subjected to the reaction}} \times 100$$

$$\text{Selectivity (\%)} = \frac{\text{Mols of the cycloolefin formed by the reaction}}{\text{Mols of the monocyclic aromatic hydrocarbon consumed by the reaction}} \times 100$$

In the Examples and Comparative Examples, the reaction time was set for comparison so that the conversion of the monocyclic aromatic hydrocarbon as the starting material would be about 30%, except for a case where the catalytic activities were very low. Further, "wt %" means "% by weight".

EXAMPLE 1

Preparation of carrier 8.0 g of a silica carrier (CARIACT 50, tradename, manufactured by Fuji Silicia Kagaku K.K., average particle size: 50 μm, specific surface area: 70 m²/g, volume of pores having pore diameters of from 250 to 1,500Å is 95% of the total pore volume of pores having pore diameters of from 75 to 150,000 Å, volume of pores having pore diameters of 350 to 1,500 Å is 85% of the total pore volume of pores having pore diameters of 75 to 150,000Å) was added to an aqueous solution having 0.87 g of zirconium oxynitrate dihydrate dissolved in 20 ml of deionized water, and dipped therein at room temperature. Then, water was distilled off by a rotary evaporator, and the product was dried. Then, the product was charged into a quartz glass reactor and baked at 1,000° C. for 4 hours under an air stream to obtain a silica carrier modified by 5 wt % of zirconium oxide. This carrier was analyzed by powder X-ray diffraction, and the average crystallite size of zirconium oxide was calculated by the Scherer's formula from the spread of the peak of zirconium oxide at a diffraction angle ($2\theta$) of about 30° and found to be 70 Å.

Figure 1:
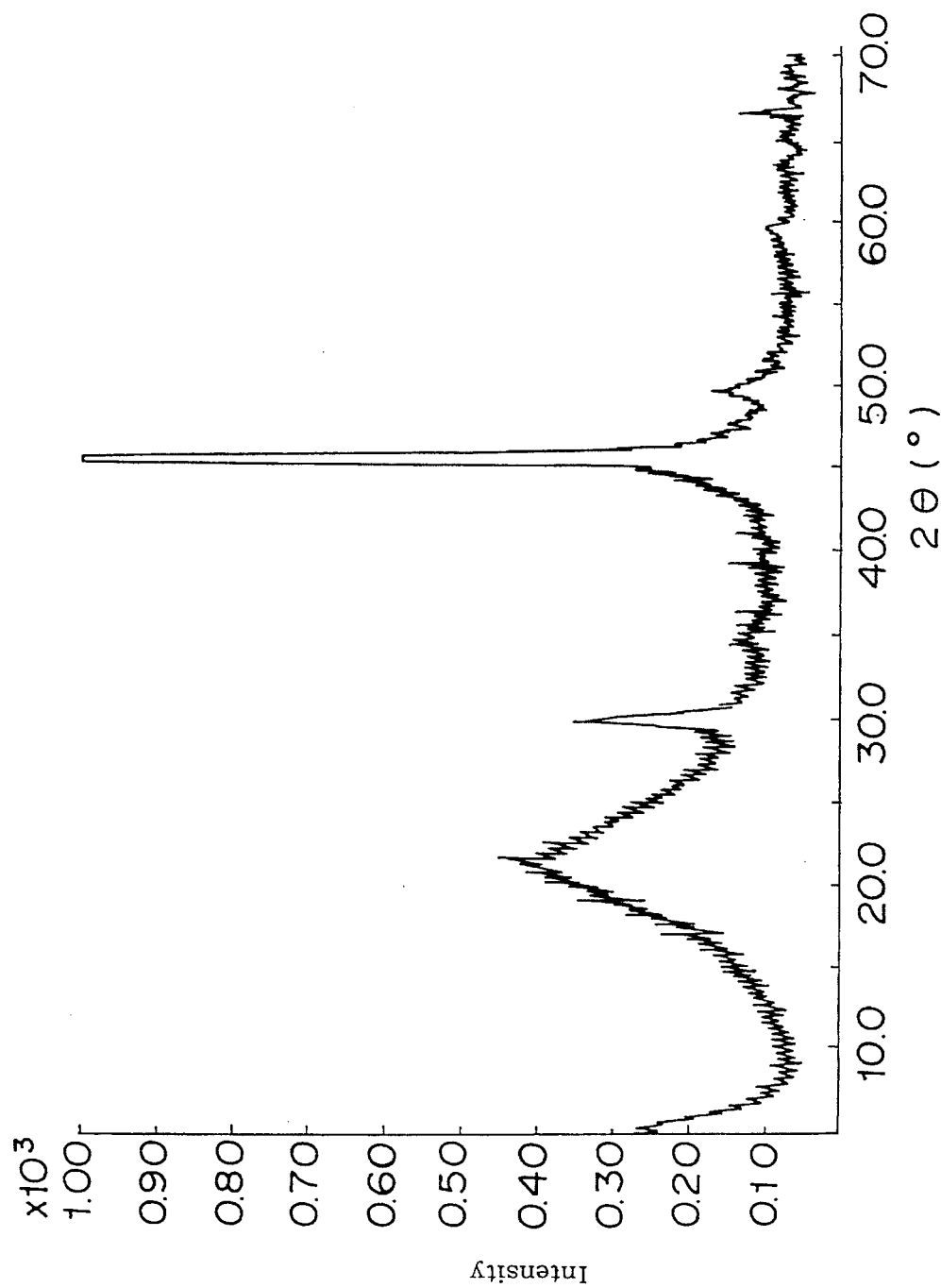
FIG. 1 is a powder X-ray diffraction pattern when the silica carrier used for the catalyst in Example 1 was heated to 1,200° C.
Figure 2:
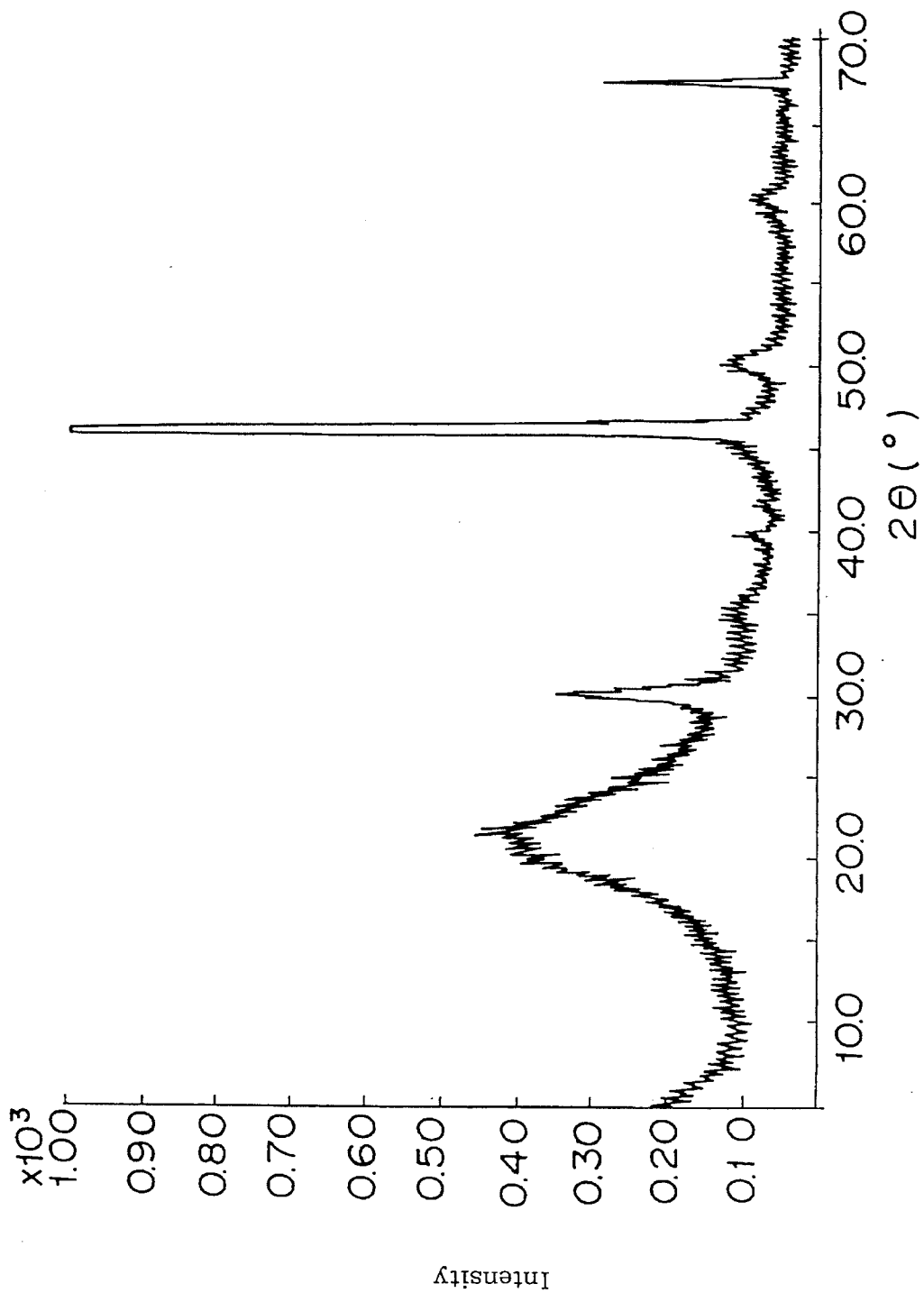
FIG. 2 is a powder X-ray diffraction pattern when the silica carrier used for the catalyst in Example 1 was cooled from 1,200° C. to 200° C.

FIG. 1 shows the powder X-ray diffraction pattern when the carrier was heated to 1,200° C. at a rate of 10° C./min from room temperature. Referring to FIG. 1, a broad peak attributable to silica is observed at $2\theta$=about 22°, and a peak attributable to the tetragonal system as a metastable phase of zirconium oxide is observed at $2=\theta$about 30°. Further, peaks at $2\theta$=about 46° and 67° are background peaks attributable to platinum used for the preparation of the test specimen for the powder X-ray analysis. Further, FIG. 2 shows the powder X-ray diffraction pattern at 200° C. when the carrier was, after heated to 1,200° C., cooled from 1,200° C. to room temperature at a rate of 10° C. /min. In FIG. 2, peaks similar to those observed in FIG. 1, are observed. From FIGS. 1 and 2, it is apparent that even when subjected to a thermal change, the carrier is stable in an amorphous state, and no crystallization of silica or no thermal transformation of zirconium oxide has taken place.

Preparation of catalyst

In an aqueous solution containing predetermined amounts of ruthenium chloride and zinc chloride, the zirconium oxide-modified silica carrier prepared in the above method was added and dipped at 60° C. for one hour. Then, water was distilled off by a rotary evaporator, and the product was dried. The catalyst (Ru/Zn (0.5/0.5 wt %)/ZrO$_2$ (5 wt %)-SiO$_2$) thus obtained, was charged into a Pylex glass tube and reduced in a hydrogen stream at 200° C. for 3 hours to activate the catalyst. The obtained catalyst was analyzed by EPMA (X-ray microanalyzer), whereby it was confirmed that ruthenium metal (Ru) was uniformly dispersed over the surface of the carrier. For the EMPA analysis, JXA-8600M manufactured by Nippon Denshi K.K. was used as the measuring apparatus, and the accelerating voltage for the electron gun was set to be 20 kV, and the probe current was set to be $2.0\times10^{-8}$ Å.

Figure 3:
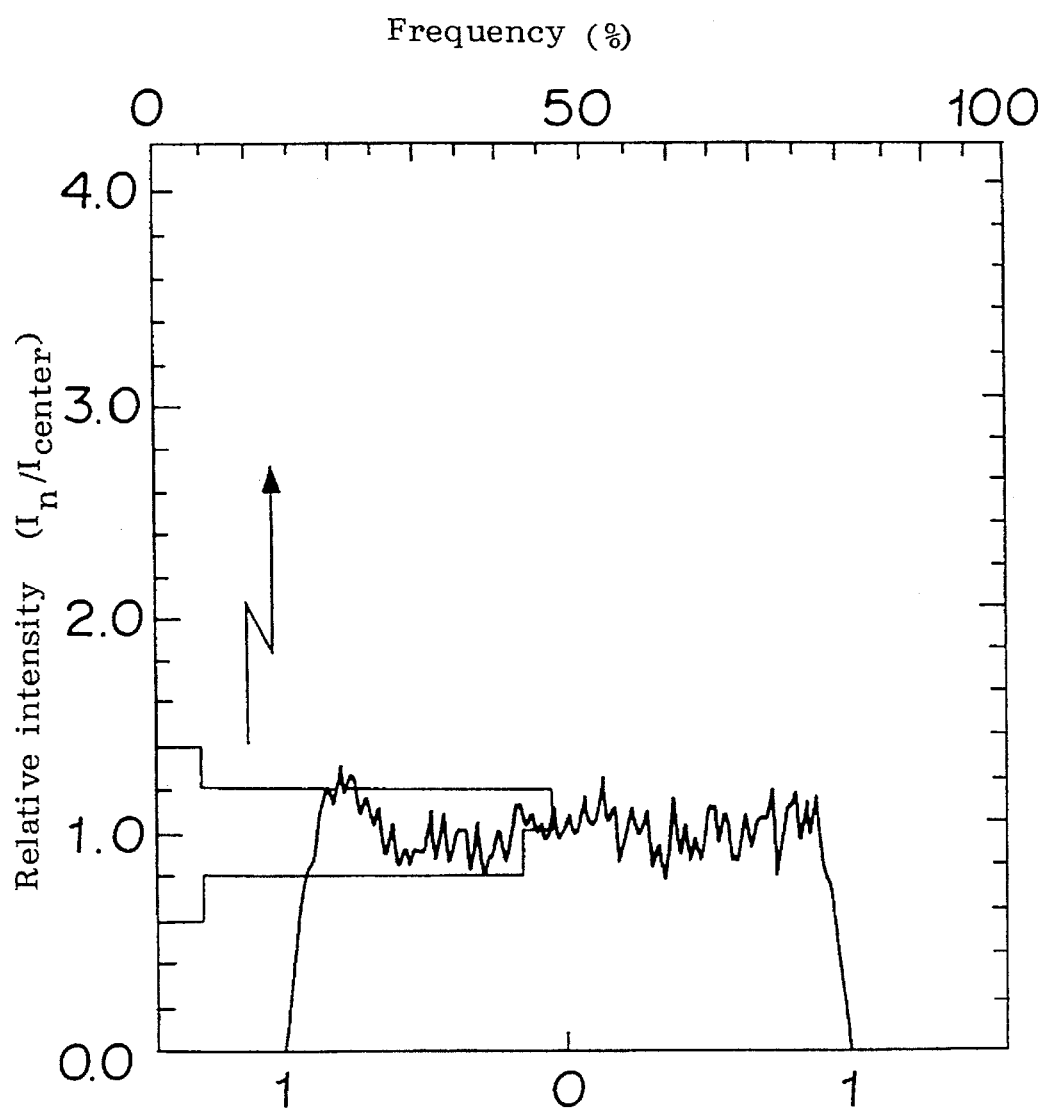
FIG. 3 is the EMPA line analysis pattern of the catalyst in Example 1.

FIG. 3 shows the EPMA line analysis pattern of the catalyst thus obtained. The unit for the lower abscissa of the EPMA line analysis pattern represents the ratio of the optional distance of the catalyst from the center of the catalyst particle to the distance of the outer surface from the center of the catalyst particle. Namely, the center is 0, and the outer surface is 1. The unit for the ordinate represents the relative intensity ($I_n/I_{center}$) of each measured point relative to the intensity ($I_{center}$) at the center of the catalyst particle. The unit for the upper abscissa represents the frequency distribution of the relative intensity in terms of the frequency factor (%). Referring to FIG. 3, with said catalyst, the relative intensity is distributed all within a range of from 0.6 to 1.4, and the relative intensity is distributed in 90% of the total within a range of from 0.8 to 1.2.

Reaction

Into a stainless steel autoclave having an internal volume of 500 ml which was preliminarily thoroughly purged with nitrogen, 120 ml of water, 14.4 g of zinc sulfate heptahydrate, 6 g of the above catalyst and 80 ml of benzene were charged. Then, hydrogen gas was introduced, and the reaction was carried out by an induction stirring method (1000 rpm) under a reaction pressure of 5.0 MPa at a temperature of 150° C. After the reaction, the autoclave was cooled, and only the oil phase was taken out, whereupon the products were analyzed by gas chromatography. The results are shown in Table 1.

Comparative Example 1

A catalyst was prepared in the same manner as in Example 1 except that instead of the zirconium oxide-modified silica carrier used in Example 1, the same silica as used in Example 1, which was not modified by zirconium oxide and which was baked in air at 1,000° C. for 4 hours, was used. The obtained catalyst was analyzed by EPMA, whereby the dispersion of Ru was found to be nonuniform as compared with the catalyst of Example 1, and segregation of Ru at the surface layer of the carrier was remarkable.

Figure 4:
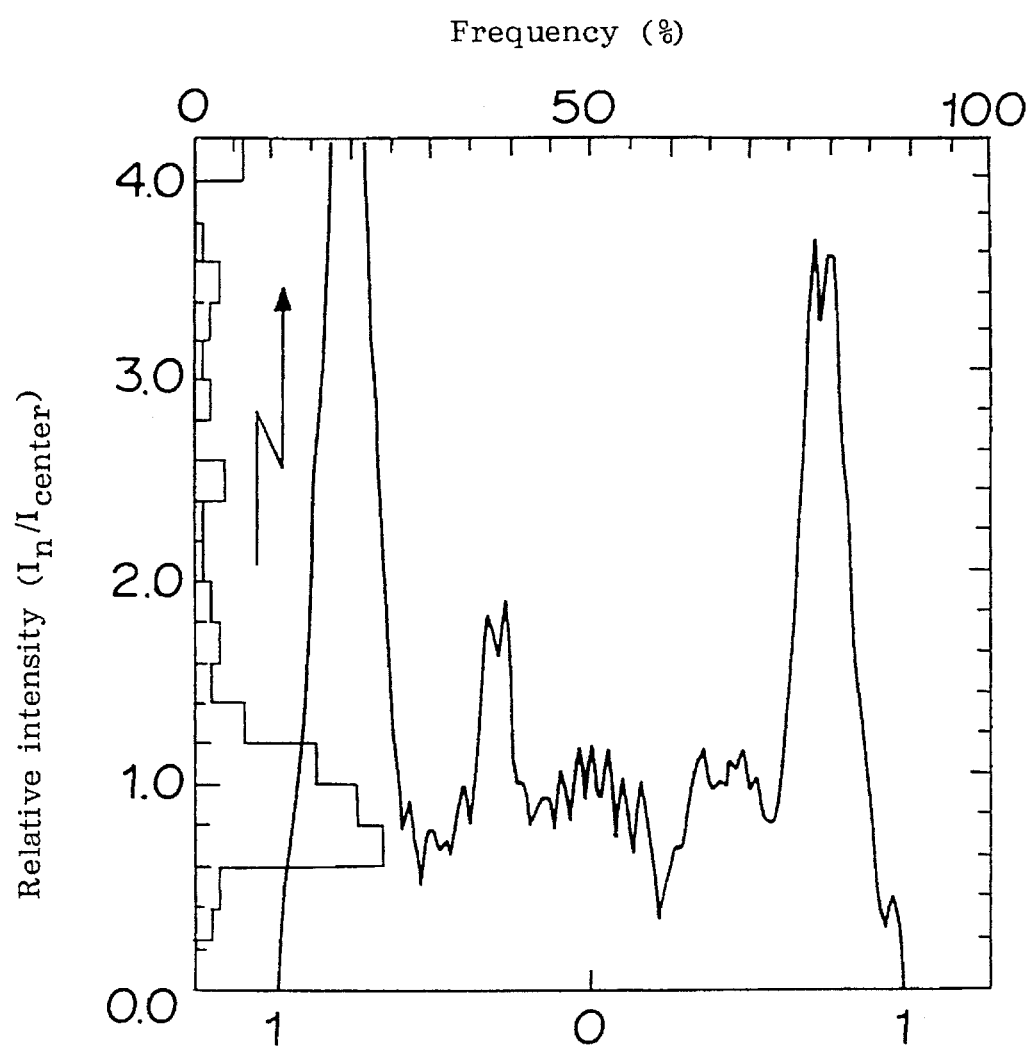
FIG. 4 is the EMPA line analysis pattern of the catalyst in Comparative Example 1.

FIG. 4 shows the EPMA line analysis pattern of the obtained catalyst. With the catalyst, some relative intensity exceeds 4, and the distribution of the relative intensity is very wide. 65% of the total is distributed within a relative intensity range of from 0.6 to 1.4, and 35% of the total is distributed within a relative intensity range of from 0.8 to 1.2.

Using this catalyst, the reaction was carried out in the same manner as in Example 1. The results are shown in Table 1. These results show that in Comparative Example 1, both the activity and the selectivity are low as compared with Example 1, thus indicating the effects of the zirconium oxide-modified silica carrier.

TABLE 1

| | Catalyst (amount of catalyst = 6 g) | Reaction time (min) | Conversion of benzene (%) | Selectivity for cyclo-hexane (%) |
| --- | --- | --- | --- | --- |
| Example 1 | Ru—Zu (0.5–0.5 wt %)/ZrO$_2$ (5 wt %)—SiO$_2$ | 60 | 58.5 | 69.2 |
| Comparative Example 1 | Ru—Zn (0.5–0.5 wt %)/SiO$_2$ | 255 | 60.2 | 59.5 |

EXAMPLE 2

The reaction was carried out in the same manner as in Example 1 except that the amount of the catalyst was changed to 3 g. However, the reaction time was set so that the conversion of benzene would be about 30%. The results are shown in Table 2.

EXAMPLE 3

The reaction was carried out in the same manner as in Example 2 except that instead of the zinc sulfate heptahydrate used in Example 2, the same weight amount of cobalt sulfate heptahydrate was used. The results are shown in Table 2.

EXAMPLE 4

A 8 wt % zirconium oxide-modified silica carrier was prepared in the same manner as in Example 1 except that the predetermined amount of zirconium oxychloride octahydrate was used as the starting material for zirconium oxide at the time of the preparation of the carrier in Example 1.

This carrier was analyzed by powder X-ray analysis, and the average crystallite size of zirconium oxide was calculated by the Scherer's formula from the spread of the peak of zirconium oxide at a diffraction angle (2θ) of about 30° and found to be 90 Å. The subsequent operation was conducted in the same manner as in Example 1 to obtain a catalyst.

Figure 5:
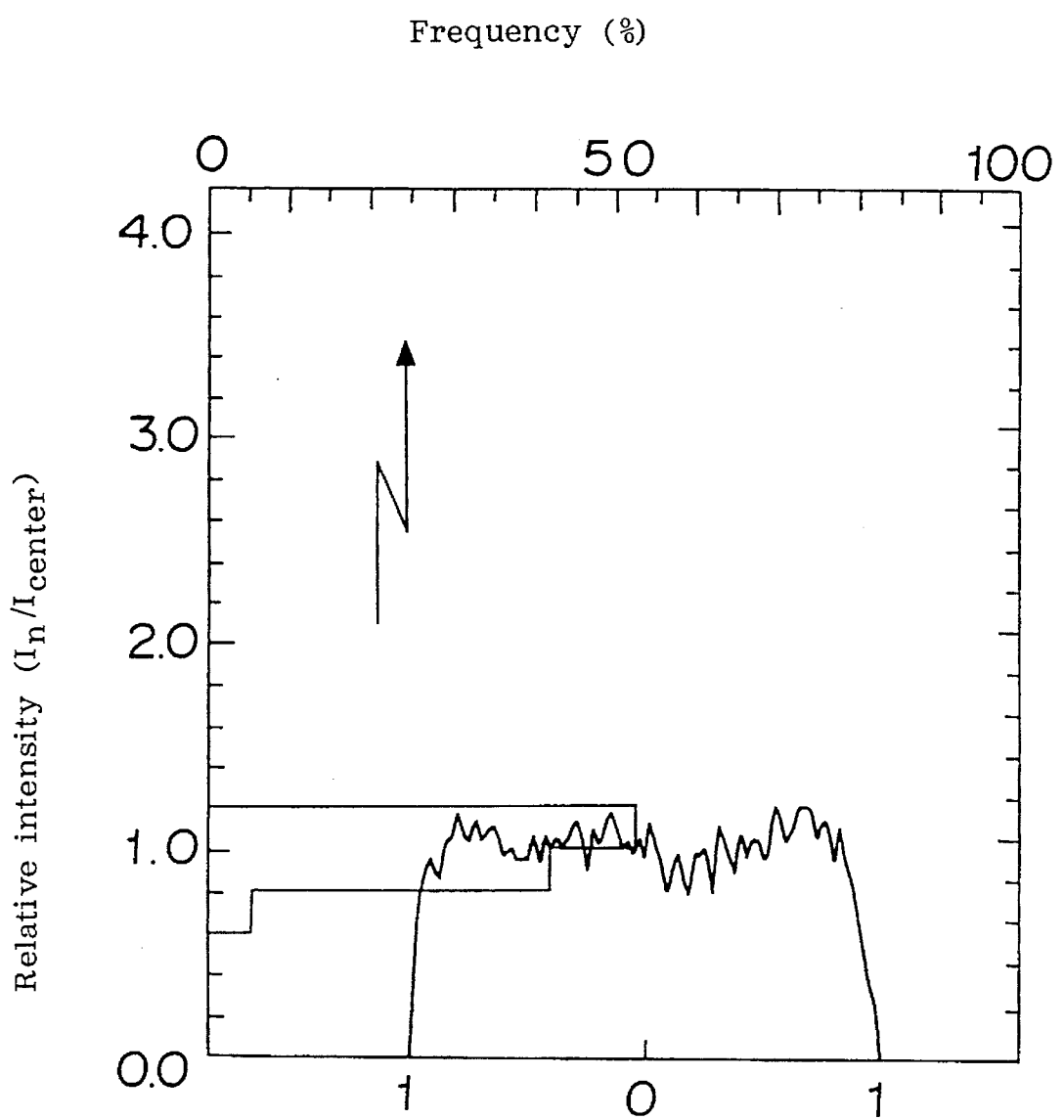
FIG. 5 is the EMPA line analysis pattern of the catalyst in Example 4.

FIG. 5 shows the EPMA line analysis pattern of the obtained catalyst. With the catalyst, the relative intensity was distributed all within a range of from 0.6 to 1.2, and 95% of the total is distributed within a relative intensity range of from 0.8 to 1.2.

Using this catalyst, the reaction was carried out in the same manner as in Example 2, the results are shown in Table 2.

Comparative Example 2

A catalyst was prepared in the same manner as in Example 1 except that instead of the zirconium oxide-modified silica carrier used in Example 1, the one prepared by adding 8 wt % of zirconium oxide to silica, physically mixing the mixture and baking it in air at 1,000° C. for 4 hours, was used as the carrier. This catalyst was analyzed by powder X-ray diffraction, and the average crystallite size of zirconium oxide was calculated from the Scherer's formula from the spread of the peak of zirconium oxide at a diffraction angle (2θ) of about 30° and was found to be 179 Å. Using this catalyst, the reaction was carried out in the same manner as in Example 2. The results are shown in Table 2.

Figure 6:
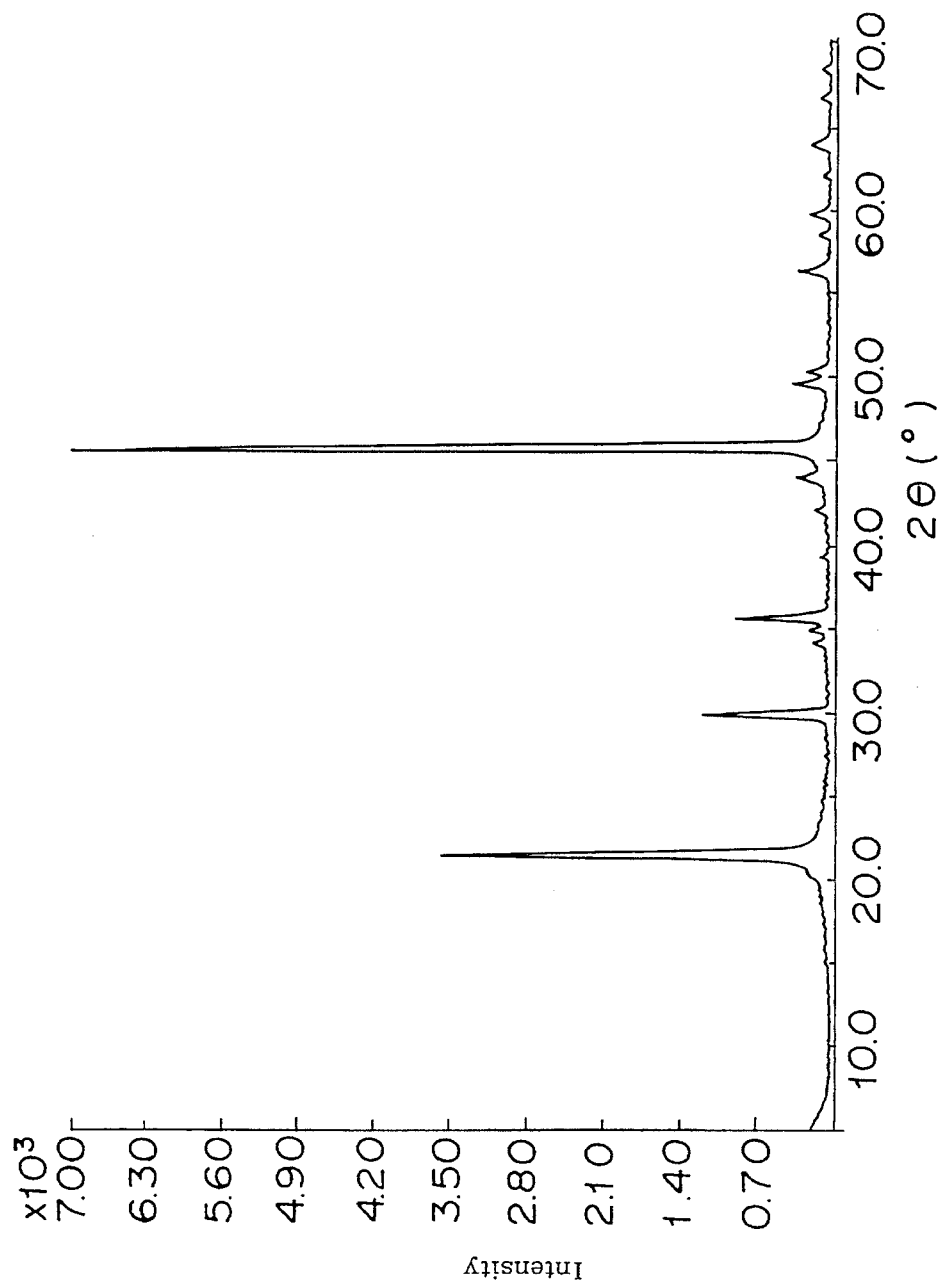
FIG. 6 is a powder X-ray diffraction pattern when the physical mixture of silica and zirconium oxide used for the catalyst in Comparative Example 2 was heated to 1,200° C.

Further, as a reference, the powder X-ray diffraction pattern when the physical mixture of silica and zirconium oxide before modification by zirconium oxide was heated from room temperature to 1,200° C., is shown in FIG. 6. Further, FIG. 7 shows the powder X-ray diffraction pattern at 200° C. when the mixture was, after heated to 1,200° C., cooled to room temperature from 1,200° C. In each of FIGS. 6 and 7, a sharp peak attributable to silica is observed at 2θ=about 22°, whereby it is apparent that silica was crystallized. Further, the peak at 2θ=about 30° indicating the tetragonal system as a metastable phase of zirconium oxide as shown in FIG. 6 is decreased in FIG. 7, and peaks at 2θ=about 28° and 31° representing the monoclinic phase of zirconium oxide appeared, thus indicating the thermal transformation of zirconium oxide. Further, peaks at 2θ=about 46° and 67° are background peaks attributable to platinum which was used at the time of preparing the test specimen for the powder X-ray analysis.

Comparative Example 3

A catalyst was prepared in the same manner as in Example 1 except that instead of the zirconium oxide-modified silica carrier used in Example 1, the one prepared by baking zirconium hydroxide in air at 1,000° C. for 4 hours to convert it to zirconium oxide, was used as the carrier. Using this catalyst, the reaction was carried out in the same manner as in Example 2. The results are shown in Table 2.

Comparative Example 4

A catalyst was prepared in the same manner as in Example 1 except that instead of the zirconium oxide-modified silica carrier used in Example 1, the one prepared by dipping the silica used in Example 1 in a commercially available zirconia sol solution (manufactured by Nissan Chemical Industries Ltd.), followed by filtration, washing with water, drying and baking in air at 1,000° C. for 4 hours, was used as a carrier. Further, this carrier was subjected to fluorescent X-ray analysis to determine the amount of zirconium oxide, whereby the amount of zirconium oxide was found to be 25 wt % relative to silica. This carrier was analyzed by powder X-ray diffraction, and the average crystallite size of zirconium oxide was calculated by the Scherer's formula from the spread of the peak of zirconium oxide at a diffraction angle (2θ) of about 30°, and was found to be 226 Å. Using this catalyst, the reaction was carried out in the same manner as in Example 2. The results are shown in Table 2.

TABLE 2

| | Catalyst (amount of catalyst = 3 g) | Reaction time (min) | Conversion of benzene (%) | Selectivity for cyclohexane (%) |
|---|---|---|---|---|
| Example 2 | Ru—Zn (0.5–0.5 wt %)/ZrO$_2$ (5 wt %)—SiO$_2$ | 42 | 28.2 | 81.3 |
| Example 3* | Ru—Zn (0.5–0.5 wt %)/ZrO$_2$ (5 wt %)—SiO$_2$ | 30 | 28.5 | 78.6 |
| Example 4 | Ru—Zn (0.5–0.5 wt %)/ZrO$_2$ (8 wt %)—SiO$_2$ | 27 | 27.7 | 75.2 |
| Comparative Example 2 | Ru—Zn (0.5–0.5 wt %)/ZrO$_2$ (8 wt %)—SiO$_2$ (Physical mixture) | 87 | 28.7 | 71.8 |
| Comparative Example 3 | Ru—Zn (0.5–0.5 wt %)/ZrO$_2$ | 27 | 26.5 | 60.7 |
| Comparative Example 4 | Ru—Zn (0.5–0.5 wt %)/ZrO$_2$ (25 wt %)—SiO$_2$ | 37 | 29.7 | 70.7 |

*In Example 3, cobalt sulfate was used as an additive instead of zinc sulfate.

EXAMPLE 5

7 g of the catalyst prepared in Example 1 and 30 g of an aqueous solution containing 6 wt % of zinc sulfate were charged into an autoclave, and contact treatment was carried out for 5 hours while stirring at a temperature of 200° C. under a hydrogen pressure of 5.0 MPa. After the treatment, the autoclave was cooled, and the catalyst was taken out, washed with water, dried and then subjected to reduction treatment in a hydrogen stream at 200° C. for 2 hours.

Using the above catalyst, the reaction was carried out in the same manner as in Example 1 except that the amount of the catalyst in Example 1 was changed to 6 g. The results are shown in Table 3.

EXAMPLE 6

7 g of the catalyst prepared in Example 1 and 30 g of an aqueous solution containing 6 wt % of lithium sulfate were charged into an autoclave, and contact treatment was carried out for 5 hours while stirring at a temperature of 150° C. under a hydrogen pressure of 5.0 MPa. After the treatment, the autoclave was cooled, and the catalyst was taken out, washed with water, dried and then subjected to reduction treatment in a hydrogen stream at 200° C. for 2 hours.

Using the above catalyst, the reaction was carried out in the same manner as in Example 5. The results are shown in Table 3.

TABLE 3

| | Metal salt for treating the catalyst | Reaction time (min) | Conversion of benzene (%) | Selectivity for cyclohexene (%) |
|---|---|---|---|---|
| Example 5 | zinc sulfate | 34 | 62.6 | 77.8 |
| Example 6 | lithium sulfate | 27 | 62.9 | 77.5 |

EXAMPLE 7

A catalyst was prepared in the same manner as n Example 1 except that the silica used in Example 1 was changed to the following.

Silica carrier: CARIACT 30, tradename, manufactured by Fuji Silicia Kagaku K.K., average particle size: 50 μm, specific surface area: 150 m²/g, volume of pores having pore diameters of from 250 to 1,500 Å is 60% of the total pore volume of pores having pore diameters of from 75 to 150,000 Å, volume of pores having pore diameters of from 350 to 1,500 Å is 12% of the total pore volume of pores having pore diameters of from 75 to 150,000 Å.

Using this catalyst, the reaction was carried out. Namely, into a titanium autoclave having an internal volume of 500 ml which was preliminarily thoroughly purged with nitrogen, 150 ml of water, 3.75 g of the above catalyst and 100 ml of benzene were charged. Further, hydrogen gas was introduced, and the reaction was carried out for 55 minutes by an induction stirring method (1,000 rpm) at a temperature of 150° C. under a reaction pressure of 5.0 MPa. Then, the conversion of benzene was 60.0%, and the selectivity to cyclohexane was 58.0%.

EXAMPLE 8

120 ml of water, 1 g of the catalyst prepared in Example 1 and 80 ml of benzene were charged into a stainless autoclave having an internal volume of 500 ml which was preliminarily thoroughly purged with nitrogen. Further, hydrogen gas was introduced, and the reaction was carried out by an induction stirring method (1,000 rpm) at a room temperature under a reaction pressure of 5.0 MPa. The results are shown in Table 4.

EXAMPLE 9

A 2 wt % zirconium oxide-modified silica carrier was prepared in the same manner as in Example 1 except that the predetermined amount of zirconium oxychloride octahydrate was used as the starting material for zirconium oxide at the time of preparing the carrier in Example 1. This carrier was analyzed by powder X-ray diffraction, and the average crystallite size of zirconium oxide was calculated by the Scherer's formula from the spread of the peak of zirconium oxide at a diffraction angle (2θ) of about 30° and was found to be 60 Å. The subsequent operation was carried out in the same manner as in Example 1 to obtain a catalyst.

Using the above catalyst, the reaction was conducted in the same manner as in Example 8 except that the amount of the catalyst in Example 8 was changed to 2 g. The results are shown in Table 4.

EXAMPLE 10

7 g of the catalyst prepared in Example 1 and 30 g of an aqueous solution containing 6 wt % of zinc sulfate were charged into an autoclave, and contact treatment was carried out for 5 hours while stirring at a temperature of 150° C. under a hydrogen pressure of 5.0 MPa. After the treatment, the autoclave was cooled, and the catalyst was taken out, washed with water, dried and then subjected to reduction treatment in a hydrogen stream at 200° C. for 2 hours.

Using the above catalyst, the reaction was carried out in the same manner as in Example 1 except that the amount of the catalyst in Example 8 was changed to 2 g. The results are shown in Table 4.

Comparative Example 5

Using the catalyst prepared in Comparative Example 1, the reaction was carried out in the same manner as in Example 8. The results are shown in Table 4.

Comparative Example 6

Using the catalyst prepared in the same manner as in Comparative Example 1 except that in Comparative Example 1, no zinc chloride was employed at the time of preparing the catalyst, the reaction was carried out in the same manner as in Example 8. The results are shown in Table 4.

TABLE 4

| | Catalyst | Reaction time (min) | Conversion of benzene (%) | Selectivity for cyclohexane (%) |
|---|---|---|---|---|
| Example 8 | Ru—Zn (0.5–0.5 wt %)/ZrO₂ (5 wt %)—SiO₂ | 30 | 29.4 | 58.6 |
| Example 9 | Ru—Zn (0.5–0.5 wt %)/ZrO₂ (2 wt %)—SiO₂ | 13 | 30.3 | 53.4 |
| Example 10 | Ru—Zn (0.5–0.5 wt %)/ZrO₂ (5 wt %)—SiO₂ | 10 | 33.0 | 60.1 |
| Comparative Example 5 | Ru—Zn (0.5–0.5 wt %)/SiO₂ | 180 | 4.4 | 57.8 |
| Comparative Example 6 | Ru (0.5 wt %)/SiO₂ | 2 | 32.3 | 5.9 |

As described in the foregoing, according to the method of the present invention, the activity per ruthenium metal is high in the partial hydrogenation reaction of a monocyclic aromatic hydrocarbon, and it is possible to obtain a cycloolefin in high selectivity. Further, the particle size of silica modified by zirconium oxide can be set within a desired range, and such is advantageous from the viewpoint of the industrial handling. Further, the catalyst component can be supported on the carrier in a highly dispersed state, and such is effective also from the viewpoint of peeling resistance of ruthenium metal, prevention of sintering and prolongation of the effective life of the catalyst. Furthermore, since the silica surface is modified by zirconium oxide, such is advantageous also from the viewpoint of the strength of the carrier. Thus, according to the present invention, a cycloolefin can be produced industrially advantageously.

What is claimed is:

1. A method for producing a cycloolefin, which comprises partially hydrogenating a monocyclic aromatic hydrocarbon in the presence of water and a ruthenium catalyst supported on silica having zirconium oxide in an amount of from 0.1 to 20 wt %, based on the silica, supported in a uniformly dispersed state on the entire surface of said silica, wherein the zirconium oxide has an average crystallite size of from 10 to 200 Å, and wherein the partial hydrogenation is conducted at a reaction temperature of from 50° to 250° C. under a hydrogen pressure of from 0.1 to 20 MPa.

2. The method according to claim 1, wherein the partial hydrogenation of a monocyclic aromatic hydrocarbon is conducted in the presence of a metal salt.

3. The method according to claim 1, wherein the partial hydrogenation of a monocyclic aromatic hydrocarbon is conducted in a liquid phase.

4. The method according to claim 1, wherein said silica has a particle size of from 5 to 500 μm.

5. The method according to claim 1, wherein said silica has pores such that the volume of pores having pore diameters of from 250 to 1500 Å constitutes at least 55% of the total pore volume of pores having pore diameters of from 75 to 150,000 Å.

6. The method according to claim 1, wherein said silica has pores such that the volume of pores having pore diameters of from 350 to 1,500 Å constitutes at least 55% of the total pore volume of pores having pore diameters of from 75 to 150,000 Å.

7. The method according to claim 1, wherein said zirconium oxide has an average crystallite size of from 20 to 100 Å.

8. The method according to claim 1, wherein the amount of ruthenium supported is from 0.001 to 10 wt % based on the silica modified by zirconium oxide.

9. The method according to claim 1, wherein the catalyst is such that the maximum value of relative intensity, defined by $I_n/I_{center}$ of ruthenium as obtained by a line analysis method by an X-ray microanalyzer, is at most 4.

10. The method according to claim 1, wherein the catalyst has a frequency distribution of at least 60% of the total, within a range of relative intensity, defined by $I_n/I_{center}$ of ruthenium of from 0.6 to 1.4 as obtained by a line analysis method by an X-ray microanalyzer.

11. The method according to claim 1, wherein the catalyst has a frequency distribution of at least of 65% of the total, within a range of relative intensity, defined by $I_n/I_{center}$ of ruthenium of from 0.8 to 1.2 as obtained by a line analysis method by an X-ray microanalyzer.

12. The method according to claim 1, wherein the catalyst is such that at least one member selected from the group consisting of zinc, iron, cobalt, manganese, gold, lanthanum and copper, is co-supported in an amount of from 0.01 to 20 by atomic ratio to ruthenium.

13. The method according to claim 1, wherein the catalyst is the one activated by contact treatment with an aqueous metal salt solution.

14. The method according to claim 13, wherein the catalyst is subjected to contact treatment with the aqueous metal salt solution in a hydrogen-containing atmosphere.

15. The method according to claim 1, wherein the amount of water present in the reaction system is from 0.01 to 10 by volume ratio to the aromatic hydrocarbon.

16. The method according to claim 2, wherein the metal salt is present in a weight ratio of from $1\times10^{-5}$ to 1 relative to the water.

17. The method according to claim 2, wherein the metal salt is a salt of zinc, cobalt or lithium.

18. The method according to claim 1, wherein the aromatic hydrocarbon is benzene.

* * * * *